United States Patent [19]
Cumming et al.

[11] Patent Number: 5,622,847
[45] Date of Patent: Apr. 22, 1997

[54] PROCESS FOR THE SEPARATION OF SOLID MATERIALS FROM MICROORGANISMS

[75] Inventors: Robert H. Cumming; Julie S. Watson, both of Cleveland; Paul Rees, Southampton, all of United Kingdom

[73] Assignee: Zeneca Limited, London, England

[21] Appl. No.: 433,501

[22] PCT Filed: Nov. 12, 1993

[86] PCT No.: PCT/GB93/02329

§ 371 Date: May 12, 1995

§ 102(e) Date: May 12, 1995

[87] PCT Pub. No.: WO94/11491

PCT Pub. Date: May 26, 1994

[30] Foreign Application Priority Data

Nov. 12, 1992 [GB] United Kingdom ............ 9223709

[51] Int. Cl.$^6$ .............. C08G 63/06; C12P 7/62

[52] U.S. Cl. .......... 435/135; 435/146; 435/252.1; 435/829; 435/872

[58] Field of Search .............. 435/135, 146, 435/829, 872, 252.1

[56] References Cited

FOREIGN PATENT DOCUMENTS

| 140864 | 5/1985 | European Pat. Off. . |
|---|---|---|
| 145233 | 6/1985 | European Pat. Off. . |
| 208805 | 1/1987 | European Pat. Off. . |
| 9118995 | 12/1991 | WIPO . |

*Primary Examiner*—Herbert J. Lilling
*Attorney, Agent, or Firm*—Cushman Darby & Cushman IP Group Pillsbury Madison & Sutro LLP

[57] ABSTRACT

Solid materials are separated from micro organisms by a process which comprises growing them at a fermentation temperature, conditioning them by cooling them without freezing and then heating to above the fermentation temperature without permitting substantial recovery from the conditioning stage.

14 Claims, No Drawings

PROCESS FOR THE SEPARATION OF SOLID MATERIALS FROM MICROORGANISMS

THIS INVENTION relates to a process for the separation of solid materials from microorganisms.

It may be advantageous to separate protein from microorganisms either because the protein itself is required or because other components of the microorganisms are required to be separated from protein.

An example of the latter case is in the production of plastics materials using microorganisms. Polyhydroxyalkanoic acids (PHA) are useful plastics materials which can be produced by this means and it is necessary if they are to be produced in an acceptable state of purity to free them from other cellular material which includes proteins.

It is known to break down cells containing PHA by heat and then to solubilise and preferably to decompose proteinaceous material for example by the use of enzymes. However, there is a tendency for proteins to denature during such treatment and this may make them resistant to the action of solubilising and decomposing agents for example enzymes; they are then difficult to remove from the PHA.

The PHA is preferably a thermoplastic hydroxybutyrate polyester, which may be a copolymer comprising other hydroxyalkanoate units for example hydroxyvalerate units. Usually it will be of D(−) configuration and suitably comprises up to 30% and preferably 3 to 25% hydroxyvalerate units, the balance being preferably substantially all hydroxybutyrate units, these percentages being by weight. Its molecular weight is suitably at least 50,000 and preferably at least 100,000 for example at least 500,000.

We have now found that if microorganisms are grown in a fermentation stage at a fermentation temperature at which they multiply rapidly and are then conditioned to render them susceptible to thermal shock in a conditioning stage by cooling them substantially below the fermentation temperature, to a conditioning temperature which is preferably by at least 10° C. and more preferably by at least 20° C. below the fermentation temperature without any substantial freezing, preferably maintained at the conditioning temperature for at least 1 hour and preferably at least 3 and more preferably at least 4 hours for example 4 to 12 hours, and then subjected to a protein separation stage by heating them to a protein separation temperature 10° to 150° C. and preferably 15° to 120° C. for example 20° to 65° C. above the fermentation temperature without permitting any substantial recovery from the conditioning effect, that the separation of protein is improved compared with that obtained if no conditioning stage is provided. The fermentation, cooling and heating stages are preferably carried out in the presence of water. Thus the severity of the heat treatment and thus of the denaturing of the proteins may be less for a similar level of protein removal and/or more protein may be removed. The separated protein may be removed from the remaining cellular material immediately or after further processing. If desired protein removal may be carried out in the presence of a surfactant.

Thus the invention comprises a process in which a solid component is recovered from a microorganism which comprises growing the microorganism at a fermentation temperature, conditioning it to render it susceptible to thermal shock in a conditioning stage by cooling it substantially below the fermentation temperature without any substantial freezing, solubilising protein contained in the microorganism by heating the microorganism in water to a protein solubilisation temperature 10° C. to 150° C. above the fermentation temperature without permitting any substantial recovery from the conditioning stage and separating one or more components of the cell as solids from the protein (optionally after decomposition of the protein).

The maximum rate of heating is suitably 0.05° to 20° C. and preferably 1° to 10° C. per second and the maximum rate of cooling is suitably 0.01° to 20° C. and preferably 1° to 10° C. per second. The average heating and cooling rates will usually be lower as the rate is a function of the temperature difference between the materials heated and the source of heat.

The conditioning effect may be partly or wholly reversed by holding the microorganisms at a fermentation temperature for an undue period in the course of heating to the protein separation stage or permitting contact with larger quantities of certain ions, especially magnesium ions.

It may be desirable to break down nucleic acids in the heat treatment stage by a subsequent heat treatment stage and/or for example by treatment with a nuclease. Such treatment may be desirable in order to reduce the viscosity of an aqueous suspension of microorganism debris which contains the desired product(s).

If the desired product is a solid for example a PHA and the protein is not required, protein is preferably decomposed for example by a protease optionally after partial separation of the PHA from protein by physical means and the desired product separated from the solubilised and/or decomposed protein. If any of the protein after initial solubilisation becomes denatured and is thereby converted to a solid or if any of the protein is not solubilised treatment for example with protease to decompose protein is beneficial. In the case of a PHA separation may be effected, preferably by filtering or centrifuging after further processing.

It will be appreciated that if a nuclease is to be used this should be done before any protease is introduced.

Preferably in the production of PHA the heating stage is sufficient to solubilise part of the non PHA cell material (NPCM) in the original cells.

The process normally solubilises at least 25% and preferably at least 50%, for example at least 70% of the protein originally present in the cell.

The NPCM will generally comprise nucleic acids, lipiris and phospholipids, peptidoglycan, proteinaceous materials including glycoproteins and, in some cases lipopolysaccharides and other carbohydrates. The proteinaceous materials generally form at least 40% by weight of the NPCM.

In the production of PHA at least some of any remaining NPCM components of the cell are preferably digested, for example solubilised and/or decomposed, in one or more stages with a solubilising agent, for example a surfactant or an oxidising agent. The proteolytic enzyme (protease) may be for example pepsin, trypsin, bromelain, papain, ficin, rennin, chymotrypsin, and bacterial or fungal proteolytic enzymes or mixtures thereof. Suitable enzyme compositions are those commonly employed in "biological" washing powders.

In a digestion stage the solubilising agent may be a proteolytic enzyme and a surfactant.

Suitable surfactants are preferably anionic.

The duration of the heat treatment that is required to effect separation of protein from cells will vary with the temperature employed. While heating for at least 5 minutes, and preferably at least 10 minutes, may be required at temperatures of about 100° C., much shorter periods can be employed at higher temperatures: for example at 150° C., heating periods as short as 20 sec. can be used. Any protein separation stage employing a surfactant will normally be conducted at temperatures above 40° C. in order to effect rapid solubilisation by the surfactant.

Although a wide range of pH conditions can be employed for the heating step, the conditions are preferably near neutral, e.g. pH 6–8, to minimise the risk of degradation of the HB polymer.

If an enzyme digestion step is employed, the digestion should be conducted at a temperature below that at which the enzyme is denatured. In many cases the denaturing temperature will be below 65° C. but with some enzymes the denaturing temperature is higher and so, with such enzymes, digestion temperatures above 65° C. can be employed. It is preferred that the digestion temperature is however below 80° C. Suitably the temperature is in the range 50° to 70° C.

Where solubilisation is carried out using both a proteolytic enzyme composition and a surfactant as the process is preferably performed in stages with the surfactant digestion stage performed after the enzyme stage or stages because the enzyme composition may be de-activated by the surfactant, and if it is desired to recycle solubilised NPCM to the fermentation step used to produce the microorganism suspension, the presence of surfactant in the solubilised portion of the suspension may preclude such use.

In order to obtain further solubilisation of the NPCM, cellular material may be contacted with a phospholipase enzyme to solubilise phospholipids which generally account for about 6 to 10% by weight of the NPCM of the original cells.

Enzyme treatments are preferably carried out at a pH within the range 6.5 to 9.0 until the requisite degree of treatment has been achieved: this will normally take between 0.2 and 2 hours.

The enzyme digestion may be performed in stages, e.g. an initial treatment with one enzyme composition followed by one or more treatment stages wherein the same or a different enzyme composition is employed.

Indeed we have found that in some cases a synergistic effect is obtained using an enzyme mixture: thus providing the enzymes do not digest one another, in some cases the use of an enzyme mixture results in a higher degree of solubilisation of NPCM than if the enzymes are used alone or sequentially.

The amount of enzyme, e.g. proteolytic enzyme and/or phospholipase enzyme, required will depend on the nature and activity of the enzyme: typically the amount of proteolytic enzyme composition will be such as to provide 0.5 to 10, preferably 1 to 6, Anson units (AU) of enzyme per 100 g of NPCM in the original cells.

The activity of a proteolytic enzyme may be determined by digesting denatured haemoglobin with the enzyme for 10 minutes at 25° C. and pH 7.5. One Anson unit is the amount of enzyme that, at an initial rate, liberates per minute an amount of TCA soluble product which gives the same colour with phenol reagent as one milli equivalent of tyrosine. A detailed description of the analytical method is given in a leaflet AF4 issued by Novo Industries. Enzymes such as lysozyme may be used to solubilise peptidoglycan. The addition of a complexing agent such as ethylene diamine tetra-acetic acid to the surfactant may be advantageous in assisting solubilisation of NPCM.

We have found that in some cases where the surfactant treatment is conducted after enzymatic digestion, in particular where the heat treatment prior to enzyme digestion was not particularly severe e.g. where the temperature did not exceed 100° C., an emulsion may be formed on such surfactant treatment from which the solids can only be separated with difficulty. The addition of cationic flocculants or electrolytes to such emulsions are not particularly effective in assisting that separation. However acidification to a pH below 2, or the addition of an absorbent mineral such as Kieselguhr, can assist separation: acidification may however cause precipitation of some of the NPCM solubilised by the surfactant.

The insoluble residue remaining after the digestion step will comprise the PHA polymer together with some residual non-solubilised, NPCM.

In a preferred aspect of the invention, after solubilisation of removal of NPCM following enzymatic and/or surfactant digestion, the PHA containing material is treated with hydrogen peroxide. Where the bulk of the proteinaceous NPCM has been solubilised by proteolytic enzymes, hydrogen peroxide treatment may effect little or no further solubilisation of residual NPCM but may be desirable to remove discoloration of the PHA polymer-containing residue. Hydrogen peroxide treatment may also be beneficial by enabling the PHA polymer-containing residue to be more readily separated, e.g. by filtration from the aqueous medium.

In other cases, e.g. where proteolytic enzyme digestion has been used to solubilise only part of the proteinaceous NPCM, and/or where digestion with a surfactant has been employed, hydrogen peroxide treatment may effect removal of a further proportion of NPCM.

Where the NPCM of the PHA polymer-containing residue comprises lipids, e.g. where no digestion with a phospholipase enzyme has been employed, lipids can be removed by washing the HB polymer-containing residue with a solvent, e.g. methanol, in which the lipids are soluble but the HB polymer is insoluble. Such a solvent washing step may also be desirable as a deodorising step.

By the above procedures an insoluble residue generally containing at least 90%, preferably at least 95% and more preferably at least 99% by weight of PHA polymer may be obtained.

In some cases the product from the digestion step can be used as such, for example as a moulding material. Alternatively the HB polymer can be extracted by solvent extraction with a solvent for the HB polymer, e.g. a partially halogenated hydrocarbon such as methylene chloride, chloroform, or 1,2-dichloroethane.

EXAMPLE 1

This illustrates the disruption of a strain of *Alcaligenes eutrophus* (deposited with National Collections of Industrial and Marine Bacteria Limited (NCIMB), 23 St Machar Drive, Aberdeen AB2 1RY, Scotland, United Kingdom under Number NCIMB 40529 on 11 November 1992) by heatshock. Two level three variable factorial analysis was used to determine the effects of Storage temperature, Storage time and Heatshock temperature on the percentage of total cell protein released. It was found that all three factors were significant and that there was an interaction between storage temperature and storage time. Rheological tests were also carried out to determine the effect of cell storage at different temperatures on the conditions of DNA after subsequent heatshock.

Introduction

Cell disruption is an important stage in the separation of intracellular products from a bacterial culture. Various methods used include homogenisation, beadmilling and chemical treatment. Heatshock can be used for partial disruption or as a pre-treatment for some other technique. One of the main effects of thermal treatment is the breakdown of the permeability barrier of the cell. This can allow the leakage of intracellular materials into the suspending medium or the introduction of detergents and lytic enzymes into the cytoplasm to cause solubilisation of the cell. Heatshock can also be used to break genetic macromolecules such as DNA into smaller soluble components preventing the formation of a highly viscous gel upon release.

The mechanism of heatshock is dependent on many factors including the heating temperature, the storage conditions, cell condition and whether the cell has been grown continuously or in a batch. The extent of disruption can be quantitatively measured by the release of soluble protein into the suspending medium. Much research has been carried out into the release of intracellular components after thermal treatment [Allwood and Russell, 1968; Watson et al, 1987], this study will attempt to show that the release of components is aided by pre-treatment during storage before thermal shocking. Also the condition of DNA after heatshocking can be influenced by the manner in which the cells are stored.

Materials and Methods

1 Protein Release

Samples of cells of the Alcaligenes eutrophus H16 strain were centrifuged at 13300 g for 5 minutes before being re-suspended in a glycerol buffer [Uhlenhopp, 1975] to an optical density of approximately 10 (540 nm) 5 ml units of cell suspension were added to thin walled test tubes which were used for all tests. A two level three factor experiment was used with the following parameters, Storage time (1 hour and 6 hours), Storage temperature (10° C. and 35° C.) and Heatshock temperature (50° C. and 90° C.). The temperature of the sample was monitored by the immersion of a K-type thermocouple probe connected to a Psion Organiser II hand held computer with an SF10 Datalogger (Digitron Instrumentation). After Heatshocking, the samples were cooled on ice to prevent further damage. Heatshocked cell samples were centrifuged at 13300 g for 5 minutes to obtain a debris free supernatant. The insoluble material remaining following the temperature shock disruption procedure is believed to be substantially composed of a solid polyhydroxyalkanoate polymer comprising mainly hydroxybutyric acid residues, which is known to be produced in the cells under the growth conditions used. The supernatant was retained for soluble protein analysis by the method of Lowry. Statistical analysis was carried out using Yates algorithms and variance analysis as given by Box et al [1978].

2 Rheology

The factors used for the rheological work were storage temperature (10° or 35° C.), Storage time (1 or 2 hours and 5 or 6 hours) and incubation time at 35° C. after heatshock (0 or 35 minutes). Four storage times were necessary instead of two to allow the rheological tests which take 25 minutes to be carried out. 1 ml of lysing solution (2% Sodium Dodecyl Sulphate, 0.02 M EDTA-$Na_2$, 0.25N NaOH) was added to 4 ml of heatshocked cell samples. The fluids were mixed by gentle rotation of the test tube to prevent damage to the sample as a result of high shear. The sample was analysed using a controlled stress rheometer (Carri-Med, Dorking, Surrey) which subjected the sample to a range of shear stresses between 0 and 2 $Nm^{-2}$ and measured the resulting shear rates ($s^{-1}$). The rheograms produced give a qualitative indication of the condition of the cellular DNA.

TABLE 1

Protein Released Expressed as a Percentage of the Total Cell Protein

| Storage Time | Heatshock Temperature | Stored at 1° C. | Stored at 10° C. | Stored at 35° C. |
|---|---|---|---|---|
| − | − | 4.31 | 9.74 | 4.17 |
| + | − | 20.76 | 27.42 | 6.05 |
| − | + | 18.55 | 22.68 | 15.18 |
| + | + | 35.58 | 38.12 | 14.13 |

TABLE 2

Calculated Effects and Standard Errors for the Variables Studied

| | Levels of Storage Temperature Examined | | |
|---|---|---|---|
| Effect | 1 and 10° C. | 10 and 35° C. | 1 and 35° C. |
| Av. Main Effects | 22.15 ± 0.88 | 17.19 ± 0.73 | 14.84 ± 0.72 |
| Storage time :A | 16.65 ± 1.76 | 8.49 ± 1.45 | 8.58 ± 1.44 |
| Storage temp :B | 4.69 ± 1.76 | −14.61 ± 1.45 | −9.92 ± 1.44 |
| Heatshock temp :C | 13.16 ± 1.76 | 10.68 ± 1.45 | 12.04 ± 1.44 |
| Interactions | | | |
| A × B | −0.09 ± 1.76 | −8.07 ± 1.45 | −8.16 ± 1.44 |
| A × C | −0.42 ± 1.76 | −1.30 ± 1.45 | −0.59 ± 1.44 |
| B × C | −1.36 ± 1.76 | −1.13 ± 1.45 | −2.49 ± 1.44 |
| A × B × C | −0.71 ± 1.76 | −0.17 ± 1.45 | −0.88 ± 1.44 |

Discussion

Table 1 shows evidence that the release of protein from heatshocked cells is much lower when they have been stored at 35° C. than when stored at 1° C. or 10° C. This could be due to the phospholipids in the membrane being held below their transition temperature forming a rigid structure (de Mendoza, 1983) which could be ruptured by heatshock more easily than a fluid cell membrane. Table 2 gives an indication of the significance of factors and whether they interact, As the cells stored at 1° C. and 10° C. give similar results there are no significant interactions evident but all of the factors are important individually. Comparing cells stored at 1° C. and 35° C. or 10° C. and 35° C. however shows an interaction between storage time and storage temperature in addition to the significance of the single factors. This interaction could be due to the rigid structure remaining but with a slight increase in the content of unsaturated fatty acids due to homeoviscous adaptation (Sinensky, 1974) which would weaken the structure of the wall when raised to elevated temperatures. The rheograms in contrast to the protein release indicate that when cells are stored at reduced temperatures, DNA survives heatshock in a better condition than when the cells have been stored at ambient growth temperatures, we think that this could be due to protein binding at low temperatures which protects vulnerable parts of the DNA molecule when it is heated. A similar phenomenon has been reported in Drosophila which was a 110 kDA protein which binds to nuclease sensitive sections of the DNA molecule when there is a change in temperature (Wu, 1987). Cells stored at 35° C. show severe DNA damage which is probably due to strand melting caused when the samples were taken above DNA's melting point.

References

Allwood, M. C. Russell, A. D. (1968) Thermally Induced Ribonucleic Acid Degradation and Leakage of Substances from the Metabolic Pool in Staphylococcus aureus. J. Bact. 85(2), 345–349.

Box, G. E. P., Hunter, W. G., Hunter, J. S. (1978) Statistics for Experiments; An Introduction To Design, Data Analysis And Model Building. John Wiley & Sons. pp306–351.

de Mendoza, D. Cronan. J. E. (1983) Thermal Regulation of Membrane Lipid Fluidity in Bacteria. Trends Biochem. Sci. 8, 45–52.

Sinensky, M. (1974) Homeoviscous Adaptation—A Homeostatic Process that Regulates the Viscosity of Membrane Lipids in *Escherichia coil*. Proc. Nat. Acad. Sci. US. 71(2), 522–525.

Uhlenhopp, E. L. Zimm, B. H. (1975) Viscoelastic Characterisation of Single-Stranded DNA From *Escherichia coli*. Biophysical Journal, 15, 223–232.

Watson, J. S. Cumming, R. H. Street, G. Tuffnell, J. M. (1978) Release of Intracellular Protein by Thermolysis. Separations for Biotechnology. Ed. Verrall, M. S. Hudson, M. J. Ellis Horwood pp 105–109.

Wu, C. et al. (1987) Purification and Properties of Drosophila Heat Shock Activator Protein. Science 238, 1247–1253.

EXAMPLE 2

Protein release After Storage at 1° C. and 35° C. Followed by Heatshock

Samples of cells of the *Alcaligenes eutrophus* H16 strain grown as continuous culture were centrifuged at 13400 g for 5 minutes before being resuspended in a glycerol buffer [Uhlenhopp and Zimm, 1975] to an optical density of 10 (540 mm). 5 ml units of cells were placed in thin walled test tubes which were stored in water baths at either 1° C. or 35° C. for up to 7 hours. Samples were removed every 30 minutes and were treated by heatshock at 90° C. by immersion in silica oil at 130° C. This was monitored by the immersion of a K-type thermocouple probe into the sample. This was connected to a Psion II hand held computer with an SF10 Datalogger (Digitron Instrumentation, Hertford, Hertfordshire, UK). After Heatshocking the samples were incubated at 35° C. for 30 minutes in a waterbath before being cooled on ice. Cold samples were immediately centrifuged at 13400 g for 5 minutes to obtain a debris free supernatant which was stored in a refrigerator before soluble protein analysis by the method of Lowry. The insoluble material remaining following the temperature shock disruption procedure is believed to be substantially composed of a solid polyhydroxyalkanoate polymer comprising mainly hydroxybutyric acid residues, which is known to be produced in the cells under the growth conditions used.

References

Uhlenhopp, E. L. Zimm, B. H. (1975) Viscoelastic Characterisation of Single-Stranded DNA From *Escherichia coli*. Biophysical Journal 15, 223–232.

Note: It has since been determined that the incubation stage in the process will have had no effect on the effect of protein release in this process and was unnecessary as a process step.

We claim:

1. A process of producing a polyhydroxyalkanoic acid in which a solid polyhydroxyalkanoic acid is recovered from a solid polyhydroxyalkanoic acid-producing microorganism of the species *Nocardia* or *Alcaligenes* which comprises growing the microorganism at a fermentation temperature, conditioning it to render it susceptible to thermal shock in a conditioning stage by cooling it below the fermentation temperature without any substantial freezing, solubilising protein contained in the microorganism by heating the microorganism in water to a protein solubilisation temperature 10° C. to 150° C. above the fermentation temperature without permitting any substantial recovery from the conditioning stage and separating polyhydroxyalkanoic acid as a solid from the protein.

2. A process according to claim 1 in which the temperature in the conditioning stage is at least 20° C. below the temperature of the fermentation stage.

3. A process according to claim 1 in which the conditioning stage is carried out at a temperature in the range 1° C. to 15° C.

4. A process as claimed claim 1 in which the conditioning stage is continued for 4 to 12 hours.

5. A process according to claim 1 in which the temperature in the protein separation stage is 15° to 120° C. above that of the fermentation stage.

6. A process as claimed in claim 1 in which the temperature in the protein solubilisation stage is 50° to 100° C.

7. A process as claimed in claim 1 in which the protein solubilisation stage is carried out at a pH of 6 to 8.

8. A process as claimed in claim 1 in which the microorganism during or after the protein solubilisation stage is contacted with an anionic surfactant.

9. A process as claimed in claim 1 in which the polyhydroxyalkanoic acid is a polymer of hydroxybutyric acid.

10. A process as claimed in claim 9 in which the polyhydroxyalkanoic acid is a copolymer of hydroxybutyric acid and hydroxyvaleric acid.

11. A process as claimed in claim 1 in which the microorganism is of the species *Nocardia*.

12. A process as claimed in claim 1 wherein the polyhydroxyalkanoic acid is separated after decomposition of the protein.

13. A process as claimed in claim 3 wherein the conditioning stage is carried out at a temperature in the range of 1° C. to 10° C.

14. A process as claimed in claim 1 in which the microorganism is of the *Alcaligenes* species.

* * * * *